United States Patent
Oka et al.

(10) Patent No.: US 6,994,671 B2
(45) Date of Patent: Feb. 7, 2006

(54) APPARATUS AND METHOD FOR SCREENING, OLFACTORY MUCOSA STIMULATING COMPOUND FOUND BY THE SCREENING METHOD, AND THERAPEUTIC APPARATUS AND ELECTRODE SECTION FOR MEASUREMENT

(75) Inventors: Hiroaki Oka, Hirakata (JP); Ryuta Ogawa, Moriguchi (JP); Tetsuo Yukimasa, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 507 days.

(21) Appl. No.: 10/070,170

(22) PCT Filed: Jun. 25, 2001

(86) PCT No.: PCT/JP01/05426

§ 371 (c)(1),
(2), (4) Date: Mar. 5, 2002

(87) PCT Pub. No.: WO02/02009

PCT Pub. Date: Jan. 10, 2002

(65) Prior Publication Data

US 2002/0122770 A1 Sep. 5, 2002

(30) Foreign Application Priority Data

Jul. 5, 2000 (JP) ........................................ 2000-204411

(51) Int. Cl.
*A61B 5/08* (2006.01)
*A61B 5/00* (2006.01)
*A61N 1/30* (2006.01)
*A61M 31/00* (2006.01)

(52) U.S. Cl. .................... 600/303; 600/300; 604/19; 604/48

(58) Field of Classification Search ................ 600/300, 600/303, 372, 373, 377, 529; 604/19, 23, 604/26, 48, 289, 514
See application file for complete search history.

(56) References Cited

U.S. PATENT DOCUMENTS 3,885,550 A * 5/1975 MacLeod .................... 600/303
6,678,553 B2 * 1/2004 Lerner et al. ................. 604/20

FOREIGN PATENT DOCUMENTS

| EP | 0 970 702 A1 | 1/2000 |
| JP | 11-196870 | 7/1999 |

* cited by examiner

*Primary Examiner*—Max F. Hindenburg
*Assistant Examiner*—Navin Natnithithadha
(74) *Attorney, Agent, or Firm*—Snell & Wilmer, LLP

(57) ABSTRACT

A method and apparatus for readily and reliably screening olfactory mucosa stimulating compounds are provided. An olfactory mucosa stimulating compound is sprayed through an atomizing nozzle 33 to an olfactory mucosa of a rat fixed in a test animal fixing device 32. A measuring electrode portion 10 is implanted in an olfactory bulb of the rat for measuring an electrical signal generated in the olfactory bulb. Efficacy of the olfactory mucosa stimulating compound is determined based on a correlation between an electrical signal measured by the measuring electrode portion 10 when the olfactory mucosa stimulating compound is sprayed on the olfactory mucosa of the rat and a physiological response induced in the rat.

7 Claims, 11 Drawing Sheets

(a)

(b)

(c)

(a)

(b)

APPARATUS AND METHOD FOR SCREENING, OLFACTORY MUCOSA STIMULATING COMPOUND FOUND BY THE SCREENING METHOD, AND THERAPEUTIC APPARATUS AND ELECTRODE SECTION FOR MEASUREMENT

TECHNICAL FIELD

The present invention relates to a screening apparatus and a screening method for determining the efficacy of various drugs which are to be administered into organisms, such as drugs for the central nervous system, or the like, which are employed in the field of environmental science, medical science, pharmaceutical science, food science, neurophysiological science, etc. More specifically, the present invention relates to an apparatus and a method for screening for an olfactory mucosa stimulating compound that stimulates the olfactory mucosa of a test animal so as to enhance homeostasis, self-curing power, etc., of the organism. The present invention further relates to olfactory mucosa stimulating compounds which are obtained by such a screening method, a therapeutic apparatus which can produce the same effect as that of the olfactory mucosa stimulating compounds, and a measuring electrode portion which is used in the screening apparatus and the therapeutic apparatus.

BACKGROUND ART

In recent years, environmental changes caused by environmental pollution have endangered the ecosystem, and new diseases have been increasing. However, due to developments in medical technology, various diseases have been overcome, and an increased number of people have been enjoying a long lifetime. Nevertheless, on the other hand, the number of patients with diseases which induce an abnormality in brain function, such as Alzheimer's disease, Parkinson's disease, etc., has been increasing. Accordingly, still more development of drugs for recovering brain function has been demanded.

Under such circumstances, many drug manufacturers and chemical manufacturers develop novel drugs.

Such drugs are generally administered into an organism by means of oral administration, application, intravenous injection, intramuscular injection, etc. These administration methods are the same in that an administered drug is circulated through the blood stream in an organism, so as to reach an affected part, and directly acts on the affected part. Further, lead compounds and analogues thereof, which are candidates for a drug that will be commercialized in the future, also directly act on an affected part similarly to conventional drugs.

In the case of a drug which is to be administered into an organism by means of oral administration, intravenous injection, or the like, it is necessary to simulate and verify the pharmacokinetics of the administered drug, the absorption rate of the drug, and the efficiency of the drug for reaching an affected part.

Further, in the case where a drug is orally administered, the administered drug is absorbed through the stomach or the small intestine, and the absorbed drug passes through the liver, and then is circulated through the body by means of the blood stream. However, in many cases, a considerable part of the drug which has reached the liver is removed from the body through excretion or metabolism, and as a result, only a portion of the administered drug is utilized. Furthermore, when a drug is administered into a patient who has damage to any of the stomach, the small intestine, or the liver, especially a patient who has damage to the liver, the type and amount of administrable drugs are sometimes limited.

In the case of a drug for a central nervous system of the brain, the administered drug needs to pass through the blood-brain barrier before reaching the inside of the brain. Thus, some drugs cannot reach the inside of the brain due to their chemical structures. Furthermore, since nerve cells having different characteristics are in a complex arrangement inside the brain, unexpected side effects can be caused by a drug that has reached the inside of the brain. It is very difficult to avoid emergence of such side effects.

In the case where a drug reaches an affected part after having been circulated in the body by means of the blood stream, a long time period elapses from when the drug is administered into the body to when the drug reaches and acts on the affected part.

Even when a drug is directly applied to an affected part so that the drug directly acts on the affected part, it is difficult to avoid the above problems.

On the other hand, it has been known that stimulation of the olfactory mucosa is directly transmitted to brain cells, but it is not necessarily clearly elucidated how the brain cells function in response to the stimulation of the olfactory mucosa.

DISCLOSURE OF THE INVENTION

The present invention was conceived in consideration of the above problems, and an objective thereof is to provide: an apparatus and a method for screening a compound which directly acts on brain cells by stimulating the olfactory mucosa; a measuring electrode portion used in such an apparatus; a stimulator which is obtained by the screening method; and a therapeutic apparatus.

In order to solve the above problems, an exemplary olfactory mucosa stimulating compound screening apparatus of the present invention includes: an administration means for administering an olfactory mucosa stimulating compound toward an olfactory mucosa of a test animal; a measuring electrode portion implanted in an olfactory bulb of the test animal for measuring an electrical signal generated in the olfactory bulb; a processing means for analyzing a correlation between an electrical signal measured by the measuring electrode portion when the olfactory mucosa stimulating compound is administered to the olfactory mucosa of the test animal by the administration means and a physiological response induced in the test animal.

An exemplary olfactory mucosa stimulating compound screening apparatus is characterized in that, in the olfactory mucosa stimulating compound screening apparatus above, the processing means directly obtains data concerning the physiological response from the test animal, so as to analyze the correlation between the physiological response and the electrical signal obtained by the measuring electrode portion.

An exemplary olfactory mucosa stimulating compound screening apparatus is characterized in that, in the olfactory mucosa stimulating compound screening apparatus above, the processing means previously stores data concerning an electrical signal in the olfactory bulb which induces a physiological response in the test animal, and analyzes based on the data the correlation between a physiological response and an electrical signal obtained by the measuring electrode portion.

An exemplary olfactory mucosa stimulating compound screening apparatus is characterized in that, in the olfactory mucosa stimulating compound screening apparatus above, the administration means includes a box for containing the olfactory mucosa stimulating compound, and a nozzle for spraying the olfactory mucosa stimulating compound contained in the box in the vicinity of the olfactory mucosa of the test animal.

An exemplary olfactory mucosa stimulating compound screening apparatus is characterized in that, in the olfactory mucosa stimulating compound screening apparatus above, the measuring electrode portion has at least one micro electrode for detecting an electrical signal from a nerve cell of the olfactory bulb.

An exemplary olfactory mucosa stimulating compound screening apparatus is characterized in that, in the olfactory mucosa stimulating compound screening apparatus above, the measuring electrode portion has a plurality of micro electrodes, the micro electrodes being arranged such that an electrical signal pattern generated in the olfactory bulb by administration of the olfactory mucosa stimulating compound to the olfactory mucosa of the test animal is obtained at a plurality of points.

An exemplary olfactory mucosa stimulating compound screening apparatus is characterized in that, in the olfactory mucosa stimulating compound screening apparatus above, an electrical signal which induces a physiological response in the test animal is supplied to each of the micro electrodes.

An exemplary olfactory mucosa stimulating compound screening method includes steps of: administering an olfactory mucosa stimulating compound to an olfactory mucosa of a test animal; measuring an electrical signal generated in the olfactory bulb of the test animal when the olfactory mucosa stimulating compound is administered to the olfactory mucosa of the test animal; and analyzing a correlation between the measured electrical signal and a physiological response induced in the test animal.

An exemplary olfactory mucosa stimulating compound screening method presents a correlation between an electrical signal measured by a measuring electrode portion and a physiological response induced in a test animal in the olfactory mucosa stimulating compound screening method above.

An exemplary treatment apparatus includes: a measuring electrode portion implanted in an olfactory bulb of an organism; and a means for supplying a stimulation pattern in the olfactory bulb, which induces a physiological response in the organism, to the measuring electrode portion in the form of an electrical signal pattern.

An exemplary measuring electrode portion is implanted in an olfactory bulb of a test animal for measuring an electrical signal generated in an olfactory bulb or supplying an electrical signal to the olfactory bulb, the measuring electrode portion comprising a plurality of micro electrodes, each of which detects an electrical signal from a nerve cell of the olfactory bulb, wherein the micro electrodes are arranged based on an electrical signal pattern which is generated in the olfactory bulb as a result of administration of an olfactory mucosa stimulating compound to an olfactory mucosa of the test animal.

An exemplary measuring electrode portion is characterized in that, in the measuring electrode portion above, each of the micro electrodes has an area of 1 $\mu m^2$ to 100,000,000 $\mu m^2$.

An exemplary measuring electrode portion is characterized in that, in the measuring electrode portion above, the micro electrodes are arranged in a matrix.

An exemplary measuring electrode portion is characterized in that, in the measuring electrode portion above, an interval between adjacent micro electrodes is 10 to 10,000 $\mu m$.

An exemplary measuring electrode portion is characterized in that, in the measuring electrode portion above, each of the micro electrodes is placed on a film-shaped substrate.

An exemplary measuring electrode portion is characterized in that, in the measuring electrode portion above, each of the micro electrodes has the shape of a ring, and is placed around a periphery of a through-hole formed in the substrate.

An exemplary measuring electrode portion is characterized in that, in the measuring electrode portion above, the inner diameter of the through-hole formed in the substrate is equal to or smaller than 10,000 $\mu m$.

An exemplary measuring electrode portion is characterized in that, in the measuring electrode portion above, the micro electrodes are provided on a front surface and a back surface at the same positions; each micro electrode provided on one of the surfaces of the substrate detects an electrical signal pattern which induces a physiological response in a test animal; and each micro electrode provided on the other surface of the substrate applies a signal which is the same as or different from the detected signal.

An exemplary measuring electrode portion is characterized in that, in the measuring electrode portion above, the micro electrodes are formed of any of gold, platinum, ITO, titanium nitride, copper, silver, and tungsten.

An exemplary measuring electrode portion is characterized in that, in the measuring electrode portion above, the substrate is made of a biomaterial.

An exemplary measuring electrode portion is characterized in that, in the measuring electrode portion above, the substrate is made of any of polyethylene terephthalate, teflon, silicone rubber, a semiconductor material, and electrically conductive rubber.

An exemplary measuring electrode portion is characterized in that, in the measuring electrode portion above, the micro electrode is formed at a tip of a needle-shaped conductive lead; a predetermined number of needle-shaped conductive leads are bound together such that the micro electrodes are placed with a predetermined interval, so as to form an electrode column; and a plurality of electrode columns are placed in parallel to each other with a predetermined interval therebetween.

An exemplary measuring electrode portion is characterized in that, in the measuring electrode portion above, the needle-shaped conductive lead has a diameter of 1 $\mu m$ to 1,000 $\mu m$.

An exemplary measuring electrode portion is characterized in that, in the measuring electrode portion above, the needle-shaped conductive lead is formed by covering a needle-shaped conductive material with an insulative film except for the micro electrode at the tip thereof.

An exemplary measuring electrode portion is characterized in that, in the measuring electrode portion above, the conductive material of the needle-shaped conductive lead is any of gold, platinum, ITO, titanium nitride, copper, silver, tungsten, and conductive rubber.

An exemplary measuring electrode portion is characterized in that, in the measuring electrode portion above, the insulative film that covers the needle-shaped conductive lead is any of polystyrene, acrylic resins, polycarbonate, polyimide.

An exemplary measuring electrode portion is characterized in that, in the measuring electrode portion above, the micro electrode is covered with a film of a biomaterial.

An exemplary measuring electrode portion is characterized in that, in the measuring electrode portion above, the tip of the needle-shaped conductive lead is covered with a film of a biomaterial.

An exemplary treatment method includes steps of: administering an olfactory mucosa stimulating compound to an olfactory mucosa of a test animal; measuring an electrical signal generated in an olfactory bulb of the test animal when the olfactory mucosa stimulating compound is administered to the olfactory mucosa of the test animal to obtain an electrical signal pattern; determining a correlation between the electrical signal pattern, and the type and level of a physiological response induced in the test animal by the electrical signal pattern; and supplying an electrical signal pattern, which is sufficient for generating an intended physiological response, to an olfactory bulb of the test animal in the form of a stimulation pattern.

An exemplary method as above is characterized in that the intended physiological response is a decrease in the blood pressure.

An exemplary method as above is characterized in that the intended physiological response is a decrease in the blood glucose level.

Figure 1:
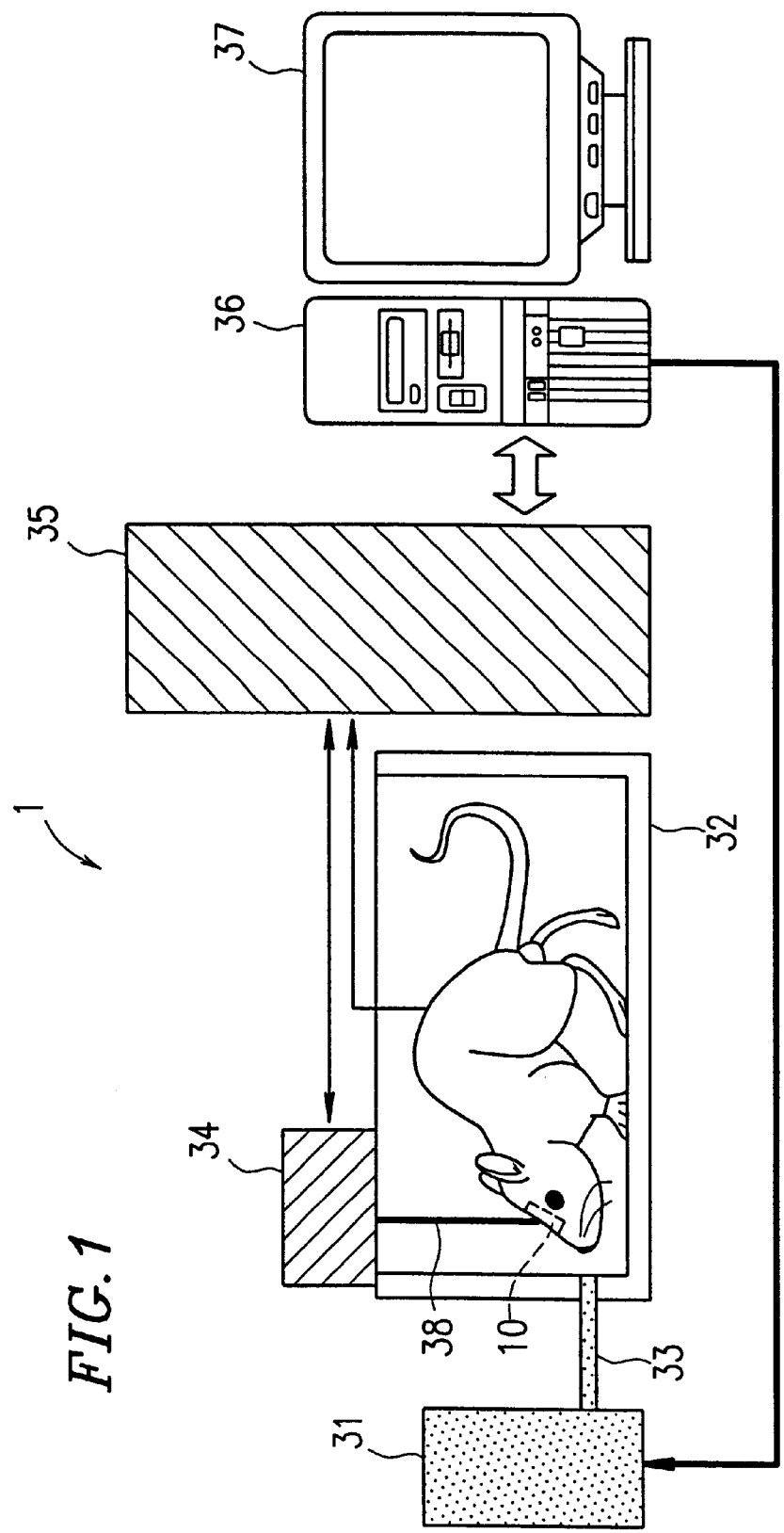
FIG. 1 is a schematic view showing an exemplary structure of a screening apparatus for screening an olfactory mucosa stimulating compound according to an embodiment of the present invention.

Reference numerals used in FIGS. 1 through 11 denote the following elements or apparatuses: 10 measuring electrode portion; 12 substrate; 13 micro electrode; 14 conductive lead; 15 power collecting section; 16 needle-shaped conductive lead; 16a micro electrode; 17 electrode column; 18 holder; 31 olfactory mucosa stimulating compound containing box; 32 test animal fixing device; 33 atomizing nozzle; 34 signal amplitude stimulating apparatus; 35 signal amplification apparatus; and 36 processing apparatus.

BEST MODE FOR CARRYING OUT THE INVENTION

The present invention relates to an apparatus and a method for screening a drug compound candidate which stimulates the olfactory mucosa of an organism so as to directly activate or suppress a brain function so that physiological functions are adjusted. The screening apparatus of the present invention measures the stimulation pattern of an olfactory bulb which is produced when an olfactory mucosa stimulating substance, which is a drug compound candidate, is administered to the olfactory mucosa of an organism. The screening apparatus then analyzes the stimulation pattern so as to examine a correlation between the stimulation pattern and a physiological response caused in the organism, whereby an olfactory mucosa stimulating substance which activates or suppresses a brain through a stimulation of an olfactory mucosa is identified.

Thus, an olfactory mucosa stimulating compound which is identified by a screening apparatus of the present invention differs from a drug which is to be orally administered, or the like, in that the compound directly stimulates brain cells through the olfactory mucosa. Therefore, such an olfactory mucosa stimulating compound is effective as a drug for treating a patient who cannot accept oral administration of a drug. Further, the olfactory mucosa stimulating compound rarely causes a side effect in a route to an affected part, which may be caused by an orally-administered drug or the like. Furthermore, it is not necessary to perform experimentation such as a pharmacokinetic experiments.

Hereinafter, a screening apparatus of the present invention is described with reference to the drawings.

FIG. 1 shows a schematic structure of a screening apparatus of the present invention. The screening apparatus 1 includes: an olfactory mucosa stimulating compound containing box 31 which is filled with an olfactory mucosa stimulating compound, which is a candidate compound to be screened, at a desired concentration; a test animal fixing device 32 for limiting the movable range of a test animal within a predetermined range; and an atomizing nozzle 33 for spraying an olfactory mucosa stimulating compound contained in the olfactory mucosa stimulating compound containing box 31 into the test animal fixing device 32.

As the test animal fixed in the test animal fixing device 32, animals of various sizes can be used according to an objective of the screening experiment. Typically, a rat, a mouse, a rabbit, or the like, is used as the test animal. The size of the test animal fixing device 32 is determined according to the size of a test animal used.

The olfactory mucosa stimulating compound filled in the olfactory mucosa stimulating compound containing box 31 is sprayed toward the tip of the nose of the test animal fixed in the test animal fixing device 32 through the atomizing nozzle 33. The test animal fixing device 32 is appropriately sized such that the olfactory mucosa stimulating compound sprayed from the atomizing nozzle 33 is not dispersed too much therein.

In this embodiment, a rat is used as the test animal, and the test animal fixing device 32 is appropriately sized based on the size of the rat.

A measuring electrode portion 10 is attached, by a surgical operation, to an olfactory bulb in the skull of the test animal fixed in the test animal fixing device 32.

The olfactory bulbs are present at the tips of olfactory tracts which extend forward from the brain. The olfactory bulbs are primary core sections of olfaction which are composed of a group of neurons arranged into a layered structure. An axon of an olfactory cell which forms an olfactory mucosa is located at the uppermost portion of a nasal cavity passes through the inside of the skull so as to reach the olfactory bulb. A secondary neuron extending from the olfactory bulb reaches an orbitofrontal gyrus, which is an olfactory area of the cerebral cortex. Thus, since stimulation of the olfactory mucosa by the olfactory mucosa stimulating compound necessarily passes through the olfactory bulb, a stimulation transmitted from the olfactory mucosa to a brain cell can be surely detected at the olfactory bulb.

The electrical response of the olfactory bulb of the test animal which is caused by spraying air that contains an olfactory mucosa stimulating compound from the atomizing nozzle 33, is measured by the measuring electrode portion 10 attached to the test animal. An electrical signal measured by the measuring electrode portion 10 is supplied to a signal amplification apparatus 35 through a terminal line 38 connected to the measuring electrode portion 10 and the signal amplitude stimulating apparatus 34. The signal amplification apparatus 35 amplifies the electrical signal obtained from the measuring electrode portion 10 and supplies the amplified signal to a processing apparatus 36 which comprises a computer or the like.

The processing apparatus 36 analyzes the stimulation pattern at the olfactory bulb based on the electrical signal obtained from the measuring electrode portion 10, and stores the stimulation pattern as data. Further, the analysis result of the stimulation pattern obtained by the processing apparatus 36 is subjected to image processing for displaying the processed stimulation pattern on a display apparatus 37.

The signal amplitude stimulating apparatus 34 located between the measuring electrode portion 10 and the signal amplification apparatus 35 is provided for amplifying an electrical signal output from the processing apparatus 36 before it is supplied to the measuring electrode portion 10. When the measuring electrode portion 10 is used for only measuring an electrical signal at the olfactory bulb, the signal amplitude stimulating apparatus 34 is not activated, so that only an electrical signal from the measuring electrode portion 10 passes therethrough.

The test animal fixing device 32 has a means for measuring physiological responses induced in an organism, such as the blood pressure, the heart rate, etc., of the test animal fixed therein. Measurement results obtained by the measuring means are supplied to the processing apparatus 36.

Figure 2:
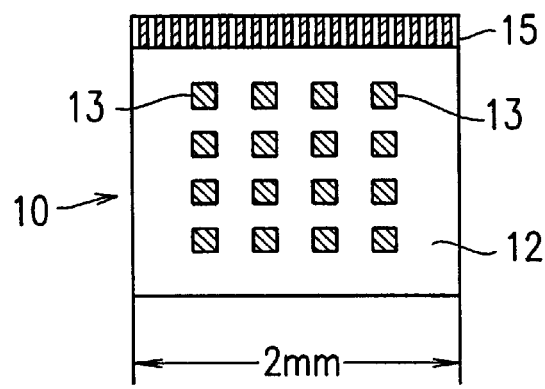
FIG. 2 shows an example of a measuring electrode which is used in a screening apparatus. Section (a) is a schematic top view showing an example of a measuring electrode portion which is used in the screening apparatus; section (b) is an enlarged top view showing details of the measuring electrode portion; and section (c) is a side view of the measuring electrode portion.
Figure 2:
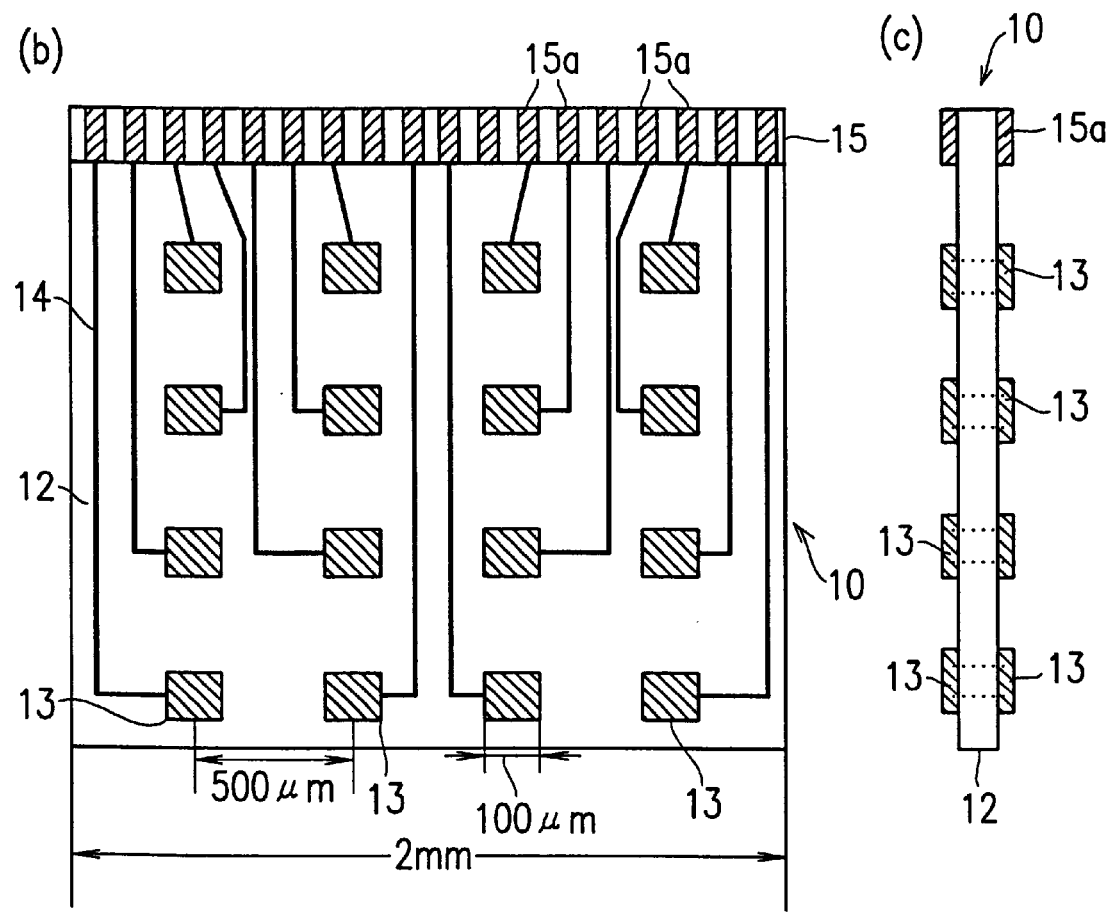
Figure 2:
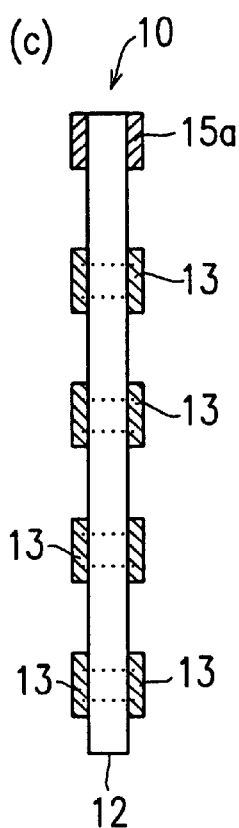

Section (a) of FIG. 2 is a schematic top view showing the measuring electrode portion 10 which is attached to the olfactory bulb of the test animal; section (b) of FIG. 2 is an enlarged view showing the measuring electrode portion 10 shown in section (a); and section (c) of FIG. 2 is a side view of the measuring electrode portion 10 shown in section (b). The measuring electrode portion 10 includes a substrate 12 formed of an insulative film, and sixteen micro electrodes 13 which are provided over the surface of the substrate 12 in the form of a 4×4 matrix, for example.

The substrate 12 has a thickness of about 1 $\mu$m to about 100 $\mu$m, and is formed into a square, each side of which is about 2 mm. Each of the micro electrodes 13 is formed into a square, each side of which is about 100 $\mu$m. The pitch between a pair of adjacent micro electrodes 13 is about 500 $\mu$m. The size of each of the micro electrodes 13 is not limited by any specific factor, but can be appropriately determined within the range of about 1 $\mu m^2$ to about 100,000,000 $\mu m^2$. The pitch between a pair of adjacent micro electrodes 13 is not limited by any specific factor, but can be appropriately determined within the range of about 10 $\mu$m to about 10,000 $\mu$m.

Each micro electrode 13 is connected with a conductive line 14. The conductive lines 14 are formed by a conductive line pattern which is provided over the substrate 12, and the surface of the conductive line pattern is covered with a film of an insulative material.

Each of the conductive lines 14 is connected to a respective one of the electrodes 15a of a power collecting section 15 which is provided along a horizontal edge of the substrate 12. Each of the electrodes 15a of the power collecting section 15 is connected to a terminal line 38 (see FIG. 1), the terminal line 38 extends from the skull of the test animal and is connected to the signal amplitude stimulating apparatus 34.

Each micro electrode 13 is covered with a thin film formed of collagen, which is a biomaterial, in order to improve the adhesiveness of the micro electrode 13 to biomedical tissue. The film covering the micro electrode 13 may be formed of a biomaterial other than collagen, such as gelatin, cellulose, or the like. Thus, when the measuring electrode portion 10 is implanted in the olfactory bulb of the test animal, the measuring electrode portion 10 is retained in the olfactory bulb with high adhesiveness to biological components of the olfactory bulb, because each micro electrode 13 is covered with a film of a biomaterial.

As the materials of each micro electrode 13 and each conductive line 14, platinum, gold, ITO, titanium nitride, copper, silver, and tungsten can be used. As the insulative material for covering the conductive lines 14, for example, polystyrene, acrylic resins, polycarbonate, polyimide, or the like, can be used.

The substrate 12 can be formed of polyethylene terephthalate, teflon, silicone rubber, a semiconductor material, or the like, but the present invention is not limited to these materials. The substrate 12 may be formed of a biomaterial, such as collagen, gelatin, cellulose, or the like. In the case where the substrate 12 is formed of a biomaterial, when the measuring electrode portion 10 is implanted in the olfactory bulb of the test animal, the substrate 12 is integrated with the biological components of the olfactory bulb, whereby the micro electrodes 13 and the conductive lines 14 covered with the films of insulative materials are retained in the olfactory bulb with high adhesiveness.

The operation of the screening apparatus 1 having such a structure is described. Firstly, an olfactory mucosa stimulating compound containing box 31 is filled with an olfactory mucosa stimulating compound, which is a candidate compound to be screened, at a desired concentration. At the same time, a rat as a test animal is fixed in the test animal fixing device 32. The measuring electrode portion 10 is attached to the olfactory bulb of the rat.

After the rat is fixed in the test animal fixing device 32, the olfactory mucosa stimulating compound, which is contained in the olfactory mucosa stimulating compound containing box 31, is sprayed together with air into the test animal fixing device 32 through the atomizing nozzle 33 toward the tip of the nose of the test animal.

The olfactory mucosa stimulating compound, which is admixed in the air sprayed from the atomizing nozzle 33, stimulates olfactory cells of the olfactory mucosa of the rat, and this stimulation is transmitted as an electrical signal to the olfactory bulb.

Each micro electrode 13 of the measuring electrode portion 10 implanted in the olfactory bulb of the rat measures an electrical signal which is generated at a corresponding position in the olfactory bulb in response to a stimulation against the olfactory mucosa. This electrical signal is transmitted to the signal amplification apparatus 35 via the conductive line 14, the power collecting section 15, and the signal amplitude stimulating apparatus 34 provided outside of the test animal fixing device 32.

The electrical signal transmitted to the signal amplification apparatus 35 is amplified by the signal amplification apparatus 35 and output to the processing apparatus 36. The processing apparatus 36 analyzes an electrical signal at a position in the olfactory bulb corresponding to each micro electrode 13 provided in the olfactory bulb based on the electrical signal obtained from the signal amplification apparatus 35.

Further, measurement results of the blood pressure, the heart rate, and the like, of the rat fixed in the test animal fixing device 32, which are obtained when the air containing the olfactory mucosa stimulating compound is sprayed from the atomizing nozzle 33, are supplied to the processing apparatus 36.

The processing apparatus 36 determines the efficacy of the olfactory mucosa stimulating compound sprayed on the rat, based on the analyzed electrical signal pattern in the olfactory bulb and the measurement results of the blood pressure, the heart rate, and the like, of the rat. For example, if a decrease in the blood pressure of the rat is detected as a result of a stimulation of the olfactory mucosa by an olfactory mucosa stimulating compound, it is determined that the olfactory mucosa stimulating compound suppresses brain cells so as to induce a physiological response that lowers the blood pressure. Accordingly, the olfactory mucosa stimulating compound is identified as a compound effective in lowering the blood pressure. In this case, the electrical signal pattern obtained by the measuring electrode portion 10 is stored as data in the processing apparatus 36.

The measuring electrode portion 10 has the sixteen micro electrodes 13 on the substrate 12, but only needs to have at least one micro electrode 13. However, in order to detect, with high resolution, the stimulation pattern which is generated in the olfactory bulb by the olfactory mucosa stimulating compound, it is desirable that a plurality of micro electrodes 13 are provided so as to obtain electrical signal patterns generated in the olfactory bulb at positions corresponding to the plurality of micro electrodes 13. In such a case, the number of the micro electrodes 13 is not limited to sixteen.

In this example, the processing apparatus 36 measures physiological responses of the rat fixed in the test animal fixing device 32, such as blood pressure, heart rate, or the like, so as to directly determine whether the physiological response is induced in the rat by the electrical signal pattern detected by the measuring electrode portion 10. However, the processing apparatus 36 may previously stores data of electrical signal patterns generated in the olfactory bulb which induce physiological responses in a test animal, and compare an electrical signal pattern to the previously stored data so as to determine whether a physiological response is induced in the rat.

Figure 3:
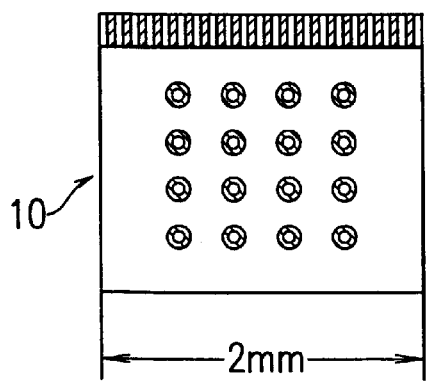
FIG. 3 shows another example of a measuring electrode which is used in a screening apparatus. Section (a) is a schematic top view showing another example of a measuring electrode portion which is used in the screening apparatus; section (b) is an enlarged top view showing details of the measuring electrode portion; and section (c) is a side view of the measuring electrode portion.
Figure 3:
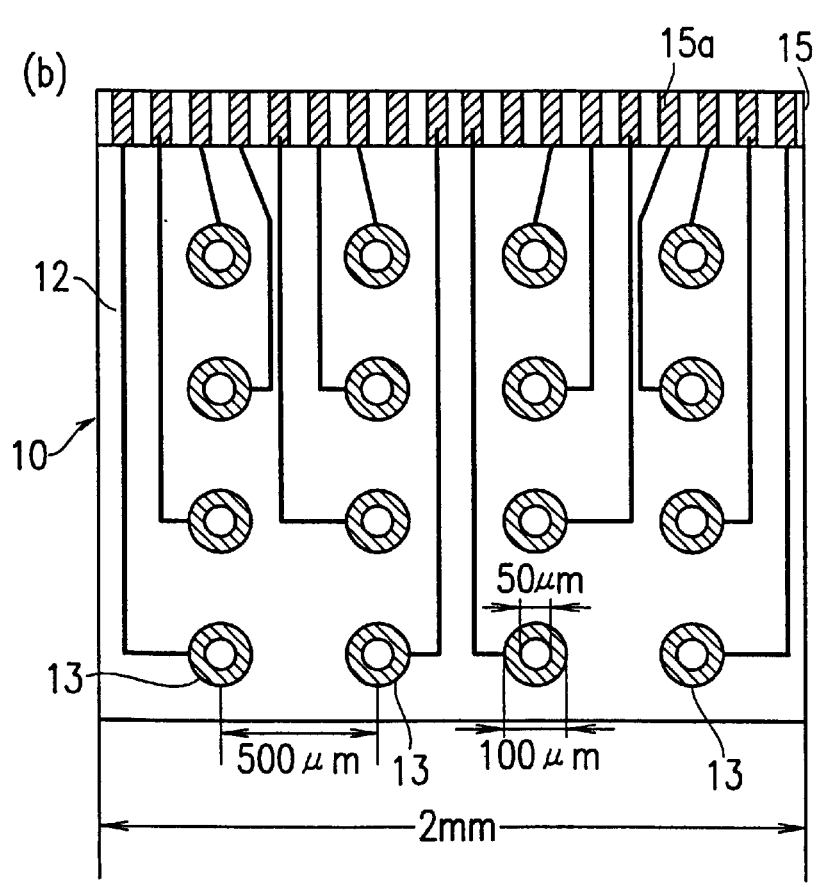
Figure 3:
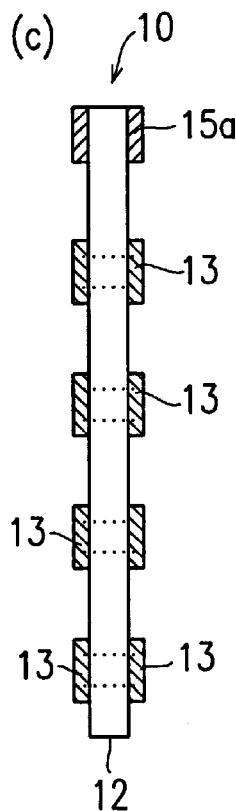

FIG. 3 shows another example of a measuring electrode portion 10. Section (a) is a schematic top view of the measuring electrode portion 10. Section (b) is an enlarged view of the measuring electrode portion 10 shown in section (a). Section (c) is a side view of the measuring electrode portion 10 shown in section (b). In the measuring electrode portion 10 of this example, over a substrate 12 formed of an insulative film material, through-holes each having an inner diameter of about 50 $\mu$m are provided in the form of a 4×4 matrix. The pitch between a pair of adjacent through-holes is about 500 $\mu$m. On the front and back surfaces of the substrate 12, a ring-shaped, micro electrode 13 is provided around the periphery of each through-hole. Thus, on each of the front and back surfaces of the substrate 12, the sixteen micro electrodes 13 are provided at the same positions.

Each micro electrode 13 has an opening having an inner diameter of about 50 $\mu$m, which is substantially the same as that of each through-hole, and is concentrically provided around each through-hole. The outer diameter of each micro electrode 13 is about 100 $\mu$m.

The inner diameters of each through-hole and the opening of each micro electrode 13 are typically within a range from 1 $\mu$m to 10,000 $\mu$m, although this depends on the outer diameter of the micro electrode 13.

Each micro electrode 13 provided on the front surface of the measuring electrode portion 10 measures an electrical signal transmitted from an olfactory cell in the olfactory mucosa to an olfactory bulb, and the measured electrical signal is supplied to the signal amplification apparatus 35 via the terminal line 38 and the signal amplitude stimulating apparatus 34. The electrical signal is amplified by the signal amplification apparatus 35 and then supplied to the processing apparatus 36. In the processing apparatus 36, the stimulation pattern in the olfactory bulb is analyzed based on the electrical signal amplified by the signal amplification apparatus 35.

Each micro electrode 13 provided on the back surface of the measuring electrode portion 10 is supplied with an electrical signal transmitted from the processing apparatus 36 which is amplified by the signal amplitude stimulating apparatus 34. The electrical signal supplied to each micro electrode 13 stimulates the olfactory bulb of the rat to which the measuring electrode portion 10 is attached. The stimulation caused by an electrical signal supplied through each micro electrode 13 is transmitted to brain cells of the rat.

For example, assume that each micro electrode 13 provided on the back surface of the measuring electrode portion 10 is supplied with an electrical signal having the same pattern as an electrical signal pattern which was obtained by each micro electrode 13 provided on the front surface of the measuring electrode portion 10 when the olfactory bulb of the rat was stimulated by an olfactory mucosa stimulating compound such that brain cells were suppressed so as to lower the blood pressure, for example. In such a case, a stimulation pattern which is the same as a stimulation of the olfactory mucosa caused by the olfactory mucosa stimulating compound, is transmitted to the brain cell through the olfactory bulb, whereby the blood pressure of the rat is lowered.

The pattern of an electrical signal supplied to each micro electrode 13 provided on the back surface of the measuring electrode portion 10 need not necessarily be the same as that obtained by the micro electrode 13 provided on the front surface of the measuring electrode portion 10 so long as the electrical signal is recognized as being effective in activating or suppressing brain cells. An electrical signal is supplied to each micro electrode 13 such that different signal patterns are obtained.

In this way, an electrical signal is supplied to each micro electrode 13 of the measuring electrode portion 10 so as to stimulates the olfactory bulb with an electrical signal having a predetermined pattern, whereby a brain cell can be activated or suppressed so as to induce a physiological response. Thus, the measuring electrode portion 10 is attached to the olfactory bulb of an organism so as to supply an electrical signal to each micro electrode 13 of the measuring electrode portion 10 such that stimulation with an electrical signal having a predetermined pattern is supplied to the olfactory bulb. As a result, brain cells are activated or suppressed such that a physiological response is induced. In this way, the apparatus of the present invention can be used as an apparatus for treating an organism.

The present invention is not limited to the measuring electrode portion 10 shown in FIG. 3 wherein the micro electrodes 13 are provided over both the front and back surfaces of the substrate 12. The measuring electrode portion 10 shown in FIG. 2 wherein the micro electrodes 13 are provided over the front surface of the substrate 12 may be used. In this case, the measuring electrode portion 10 is implanted into an olfactory bulb of a human, and a predetermined electrical signal from the processing device 36 is amplified by the signal amplitude stimulating apparatus 34 and supplied to each micro electrode 13 of the measuring electrode portion 10. In this way, a physiological response is induced in the human body, and such an apparatus can be use as an apparatus for treating a human body.

In the measuring electrode portion 10 shown in FIG. 3, each micro electrode 13 is formed so as to have the shape of a ring. The openings of the micro electrodes 13 which are formed on the front and back surfaces of the substrate 12 are in communication with each other via the through-holes formed in the substrate 12. Nerve tissue of an olfactory bulb which was disconnected when the measuring electrode portion 10 was implanted in the olfactory bulb extends through openings of a pair of micro electrodes 13 and the through-holes, so that disconnected neural pathways in the olfactory bulb can be regenerated.

Figure 4:
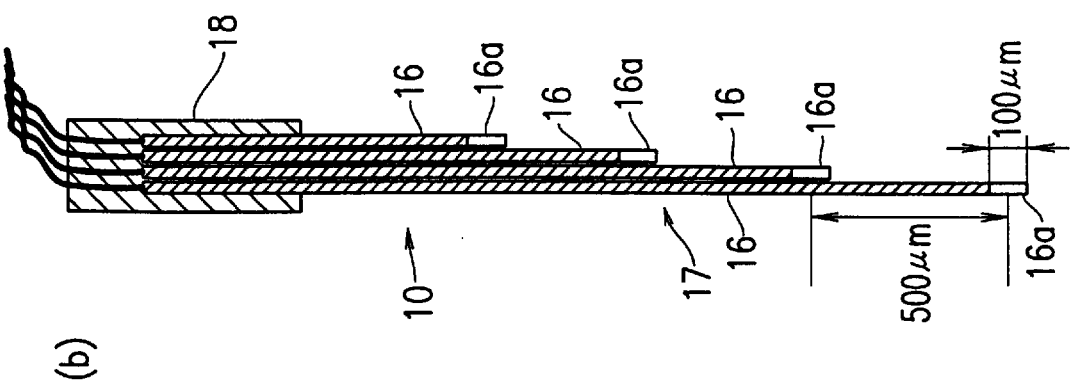
FIG. 4 shows still another example of a measuring electrode which is used in a screening apparatus. Section (a) is a schematic view showing a still another example of a measuring electrode portion which is used in the screening apparatus; and section (b) is a schematic view showing details of the measuring electrode portion.
Figure 4:
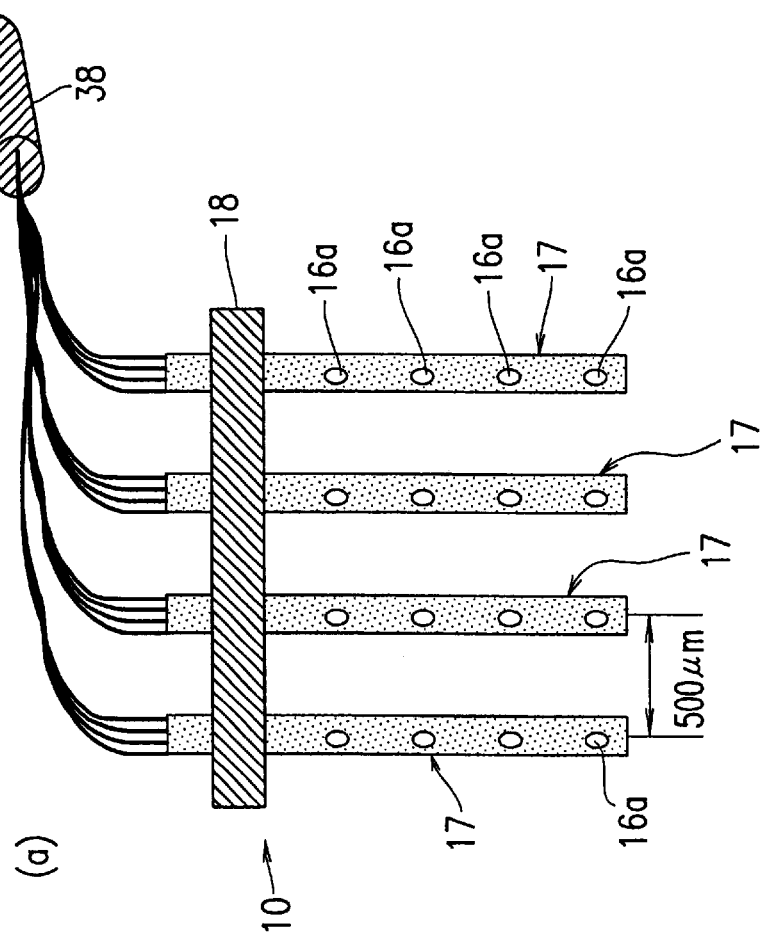

FIG. 4 shows still another example of the measuring electrode portion 10. Section (a) shows a schematic structure of the measuring electrode portion 10. Section (b) is a cross-sectional view showing a principal part of the measuring electrode portion 10. The measuring electrode portion 10 includes four electrode columns 17, each of which is formed of four needle-shaped conductive leads 16 bound together. The conductive leads 16 have different lengths, and each of the conductive leads 16 has a micro electrode 16a at a tip thereof. Each needle-shaped conductive lead 16 is formed of a needle-shaped conductive material covered with an insulative film. The insulative film is peeled at the tip of each conductive lead 16 so as to form a micro electrode 16a. Each micro electrode 16a has a length of 100 μm, for example.

As the conductive material of the conductive leads 16, platinum, gold, nickel, titanium nitride, copper, silver, tungsten, etc., can be used. As the insulative film that covers the conductive material, polyimide, polystyrene, acrylic resins, polycarbonate, or the like, can be used.

In each electrode column 17, the four needle-shaped conductive leads 16 having different lengths are bound together such that the micro electrodes 16a, which are formed at the tips of the needle-shaped conductive leads 16, are located at intervals of 500 μm. Each electrode column 17 is fixed at a position 500 μm away from the tip of the shortest needle-shaped conductive lead 16 of the electrode column 17 with an insulative holder 18 made of silicon, teflon, or the like, such that the electrode columns 17 are retained in parallel to each other with an interval of 500 μm. It should be noted that, in section (a) of FIG. 4, the width of each needle-shaped conductive lead 16 is shown as being broader than the actual width thereof, for clarity of illustration.

The measuring electrode portion 10 having such a structure is implanted in an olfactory bulb of an organism, and is used as a part of the screening apparatus shown in FIG. 1 or a treatment apparatus. Since in this measuring electrode portion 10, the electrode columns 17 each having the four micro electrodes 16a are retained with appropriate intervals therebetween, the measuring electrode portion 10 can be implanted into the olfactory bulb of the organism with reduced disconnection of the brain tissue while maintaining the neural network of the olfactory bulb.

EXAMPLES

The present invention is described by way of examples. The following examples are merely the exemplification of the present invention, but the present invention is not limited thereto.

Example 1

A two-week-old rat was used as a test animal. The measuring electrode portion 10 shown in FIG. 4 was implanted into the rat by a surgical operation.

In the measuring electrode portion 10, the length of the micro electrode 16a was 100 μm, and the interval between adjacent micro electrodes 16a in each electrode column 17 was 500 μm. Platinum was used as a conductive material for the needle-shaped conductive lead 16. Polyimide was used as the insulative film.

Before the measuring electrode portion 10 was implanted into the olfactory bulb of the rat, the micro electrodes 16a were pretreated with an N2 supplement and collagen in order to improve regeneration of nerve cells and adhesiveness of the micro electrodes 16a to the nerve cells after the implantation.

In order to attach the measuring electrode portion 10 to the rat, Nembutal (barbiturate) was injected into the abdominal cavity of the rat in a quantity equal to a ¹/₁₀ of the weight of the rat, so as to anesthetize the rat, and the anesthetized rat was fixed in the prone position. After the rat was fixed, the skin of the head of the rat was cut open at its forehead, and a hole of 1 mm×5 mm was formed in the skull. Then, the pretreated measuring electrode portion 10 was inserted into the olfactory bulb, and the terminal line 38 of the pretreated measuring electrode portion 10 was extended from the head of the rat. Next, the hole formed in the skull is filled with dental cement, and the skin of the head was sutured, with the terminal line 38 being pulled out of the skull. After having been sutured, the surgically-operated portion of the rat was cleaned with antibiotics (100 μ/ml of penicillin and 100 μg/ml of streptomycin), and was reinforced with sterilized dental cement.

After such an implantation operation of the measuring electrode portion 10, the rat was reared for three weeks under an environment which was cleaned with activated carbon so as to remove substances that produce aromas. Then, three weeks after the surgical operation, the rat was fixed in the test animal fixing device 32 of the screening apparatus 1 shown in FIG. 1. The terminal line 38, which extended from the body of the rat, was connected to the signal amplitude stimulating apparatus 34 outside the test animal fixing device 32.

Figure 5:
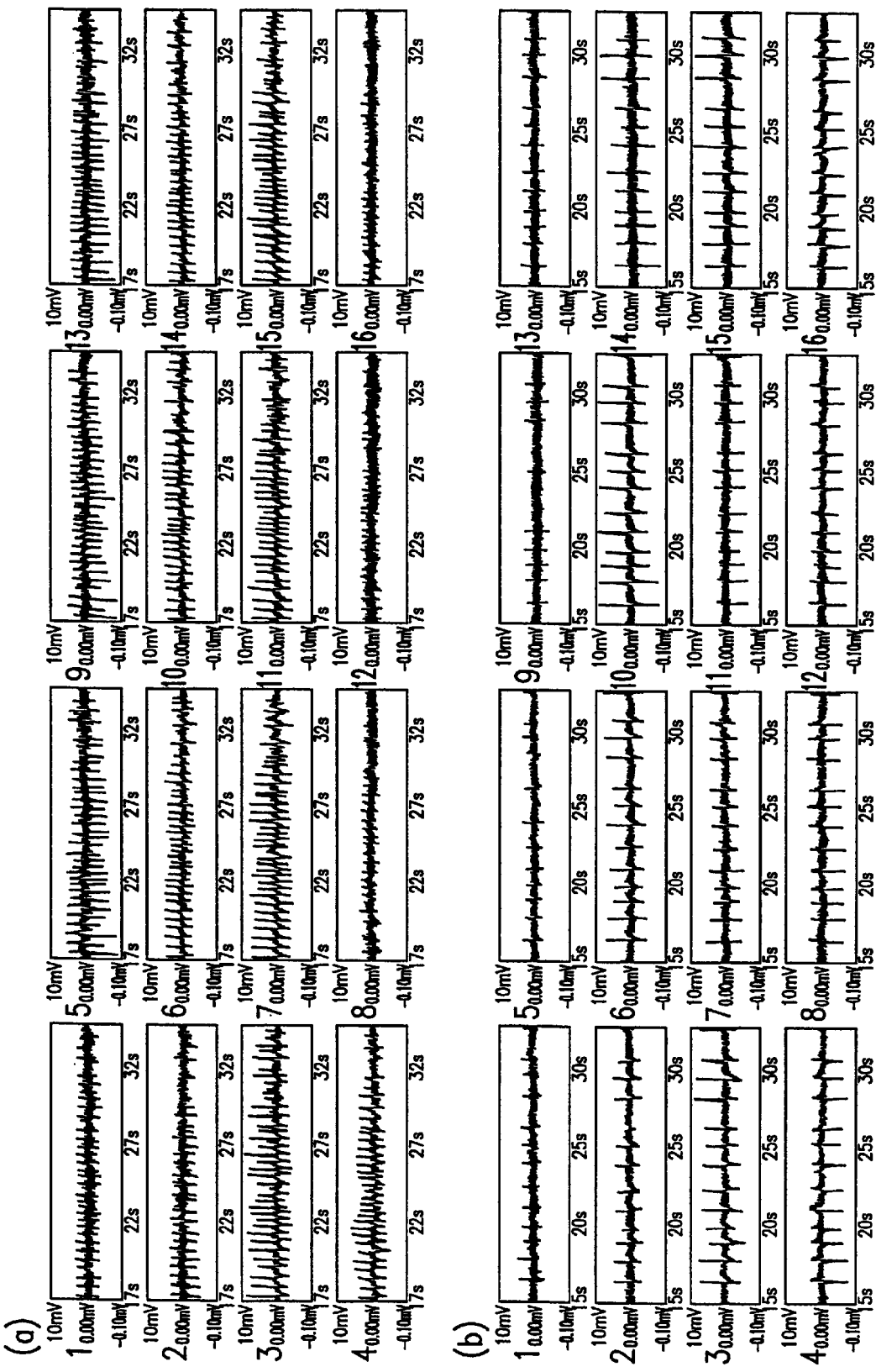
FIG. 5 shows results obtained by Example 1. Sections (a) and (b) show electrical signal patterns which were measured by a measuring electrode portion in Example 1.

In such an arrangement, a predetermined concentration of cineole ($C_{10}H_{18}O$) was introduced, as an olfactory mucosa stimulating compound, into the olfactory mucosa stimulating compound containing box 31 of the screening apparatus 1. Cineole in the olfactory mucosa stimulating compound containing box 31 was sprayed together with normal air on the rat in the test animal fixing device 32 for 5 minutes. The response induced in the olfactory bulb of the rat was recorded in the form of an electrical signal from each micro electrode 16a of the measuring electrode portion 10. Section (a) of FIG. 5 shows electrical signals obtained through the sixteen micro electrodes 16a of the measuring electrode portion 10. At the same time, the blood pressure and the heart rate of the rat were measured when cineole was sprayed on the rat. Results of the measurement are shown in section (a) of FIG. 6.

Figure 6:
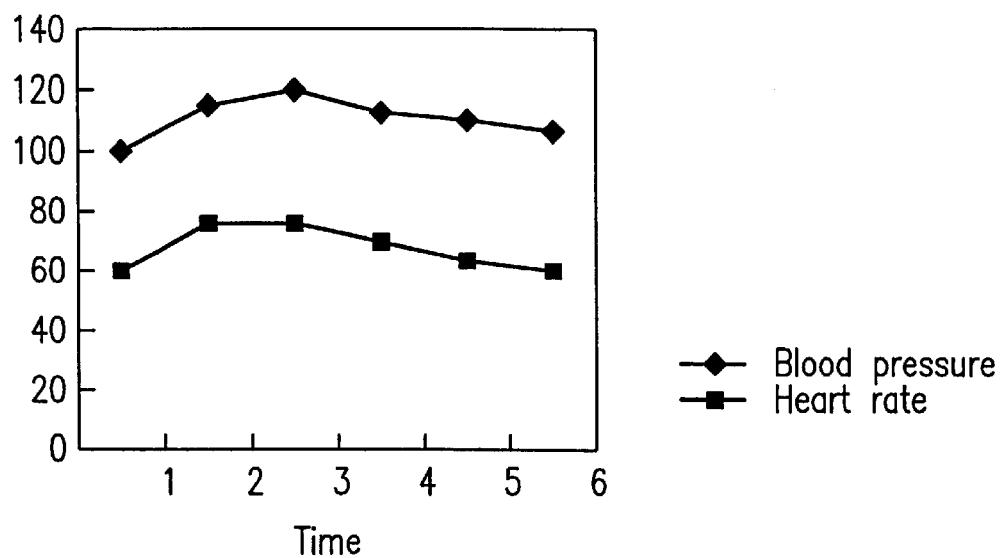
FIG. 6 is a graph showing variations of blood pressure and heart rate against time. Sections (a) and (b) show variations of the blood pressure and the heart rate against time, which were induced by the electrical signal patterns shown in sections (a) and (b) of FIG. 5, respectively.
Figure 6:
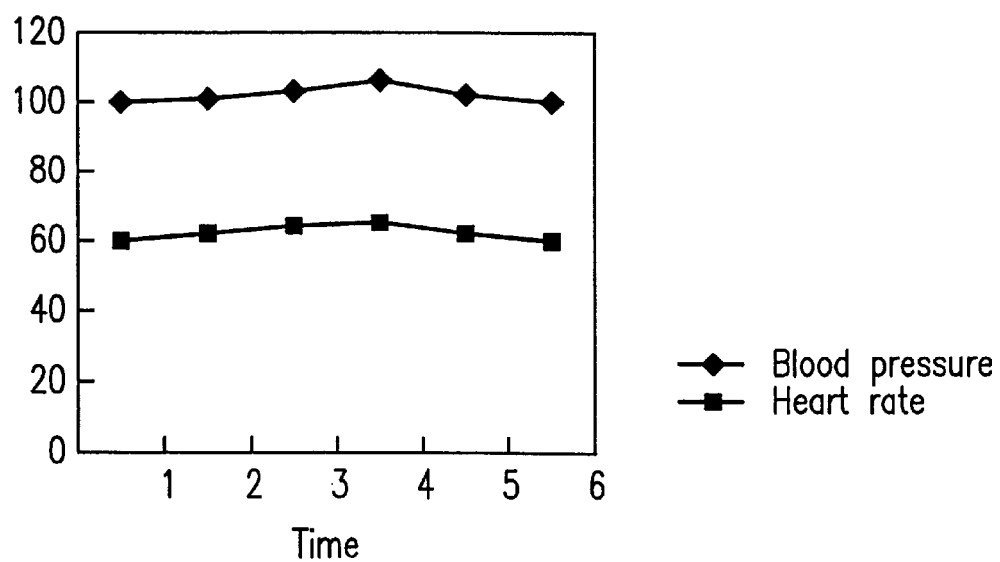

Next, air not containing cineole was cleaned with activated carbon, and the cleaned air was introduced into the test animal fixing device 32 for 30 minutes until the response of the olfactory bulb of the rat stabilized. After the olfactory bulb of the rat had stabilized, cineole was sprayed into the test animal fixing device 32 together with air at an oxygen concentration 5% higher than normal air, and a response of the olfactory bulb of the rat obtained at that time was recorded in the form of an electrical signal from each micro electrode 16a of the measuring electrode portion 10. Section (b) of FIG. 5 shows electrical signals obtained through the sixteen micro electrodes 16a of the measuring electrode portion 10. Section (b) of FIG. 6 shows the blood pressure and the heart rate of the rat which were obtained simultaneously with the electrical signals.

From a comparison between section (a) and section (b) of FIG. 5, it was confirmed that cineole stimulated the olfactory mucosa. Further, from a comparison between section (a) and section (b) of FIG. 6, it was confirmed that cineole induced physiological responses, i.e. increases in the blood pressure and the heart rate. Furthermore, it was confirmed that the blood pressure and the heart rate of the rat were increased more greatly when cineole was sprayed on the olfactory mucosa together with air at a normal oxygen concentration, rather than when cineole was sprayed on the olfactory mucosa together with air at an oxygen concentration 5% higher than normal air.

Thus, it was confirmed that cineole is effective in increasing the blood pressure and the heart rate, especially when the rat is not in a high oxygen concentration environment.

Example 2

The measuring electrode portion 10 shown in FIG. 3 was attached to a rat in a similar manner to that described in Example 1. Each ring-shaped micro electrode 13 of the measuring electrode portion 10 was made of ITO, which is a conductive material. The surface of each micro electrode 13 was plated with gold. As the substrate 12, a polyimide film material having a thickness of 100 μm was used.

The rat with the measuring electrode portion 10 attached thereto was fixed in the test animal fixing device 32 of the screening apparatus 1 shown in FIG. 1. The electrical signals shown in FIG. 7 were supplied to the respective sixteen micro electrodes 13 provided on the back surface of the measuring electrode portion 10 such that predetermined electrical signal patterns were supplied to the olfactory bulb of the rat. Variations in the blood pressure and the heart rate of the rat with the passage of time, which were caused when the electrical signal patterns were supplied to the olfactory bulb, were measured. The results of the measurement are shown in FIG. 8.

Figure 7:
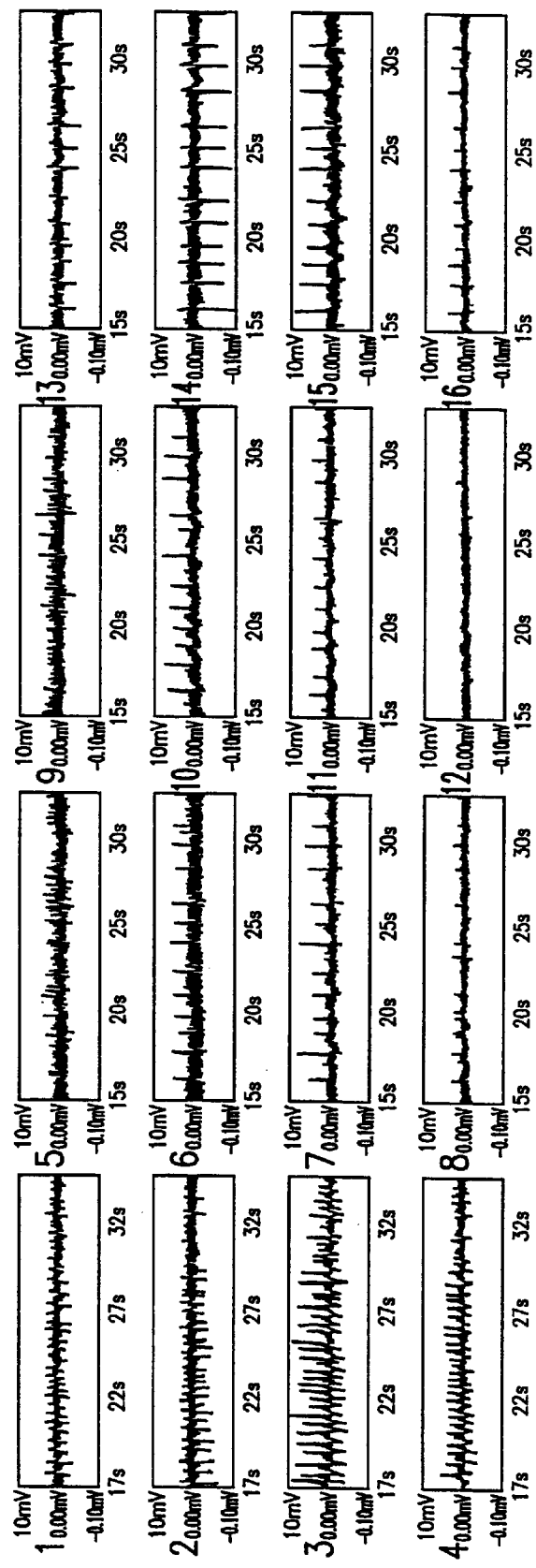
FIG. 7 shows electrical signal patterns supplied to the measuring electrode portion in Example 2.
Figure 8:
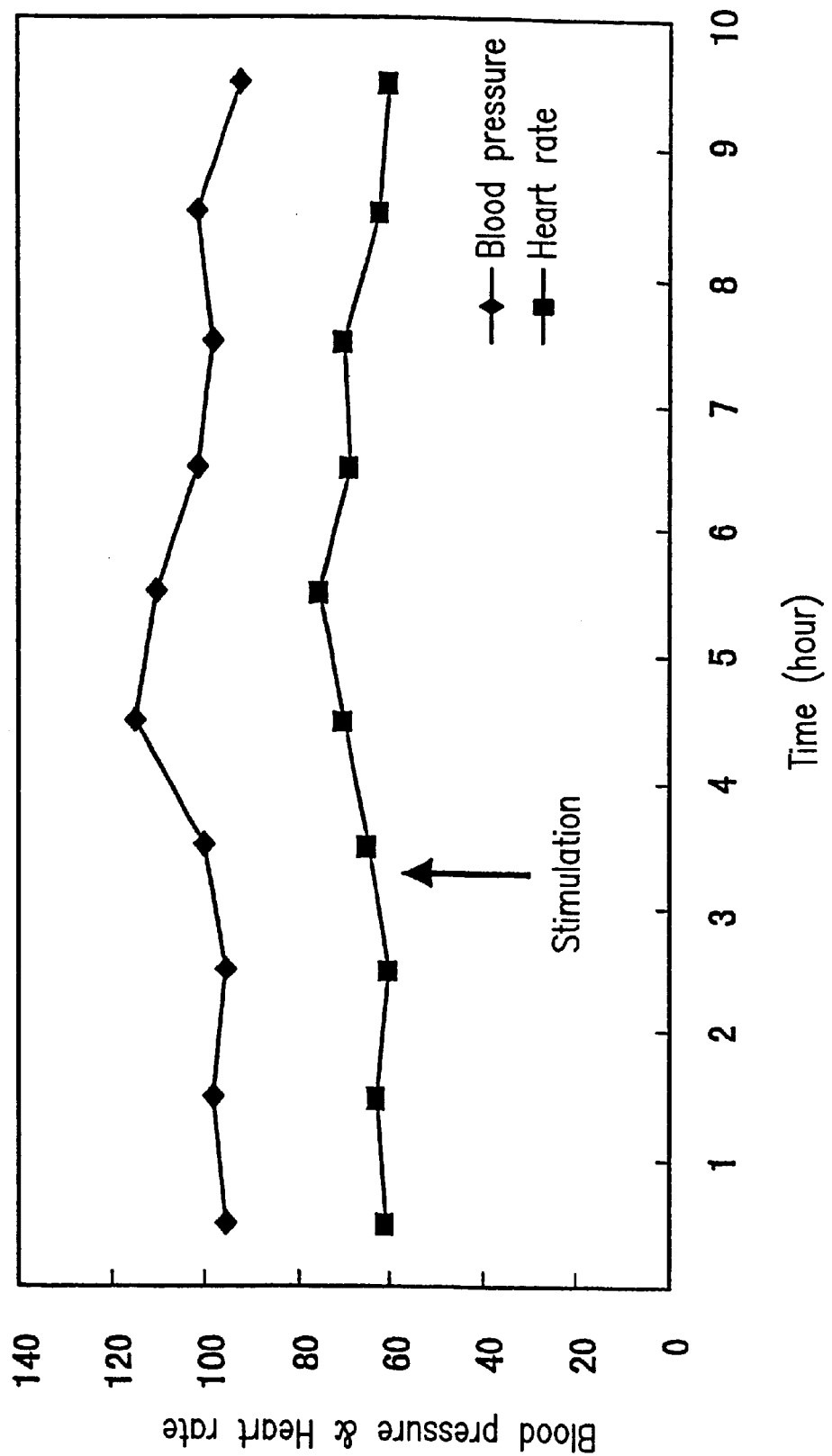
FIG. 8 is a graph showing variations of blood pressure and heart rate of a rat against time, which were obtained when the electrical signal patterns shown in FIG. 7 were supplied to the measuring electrode portion.
Figure 9:
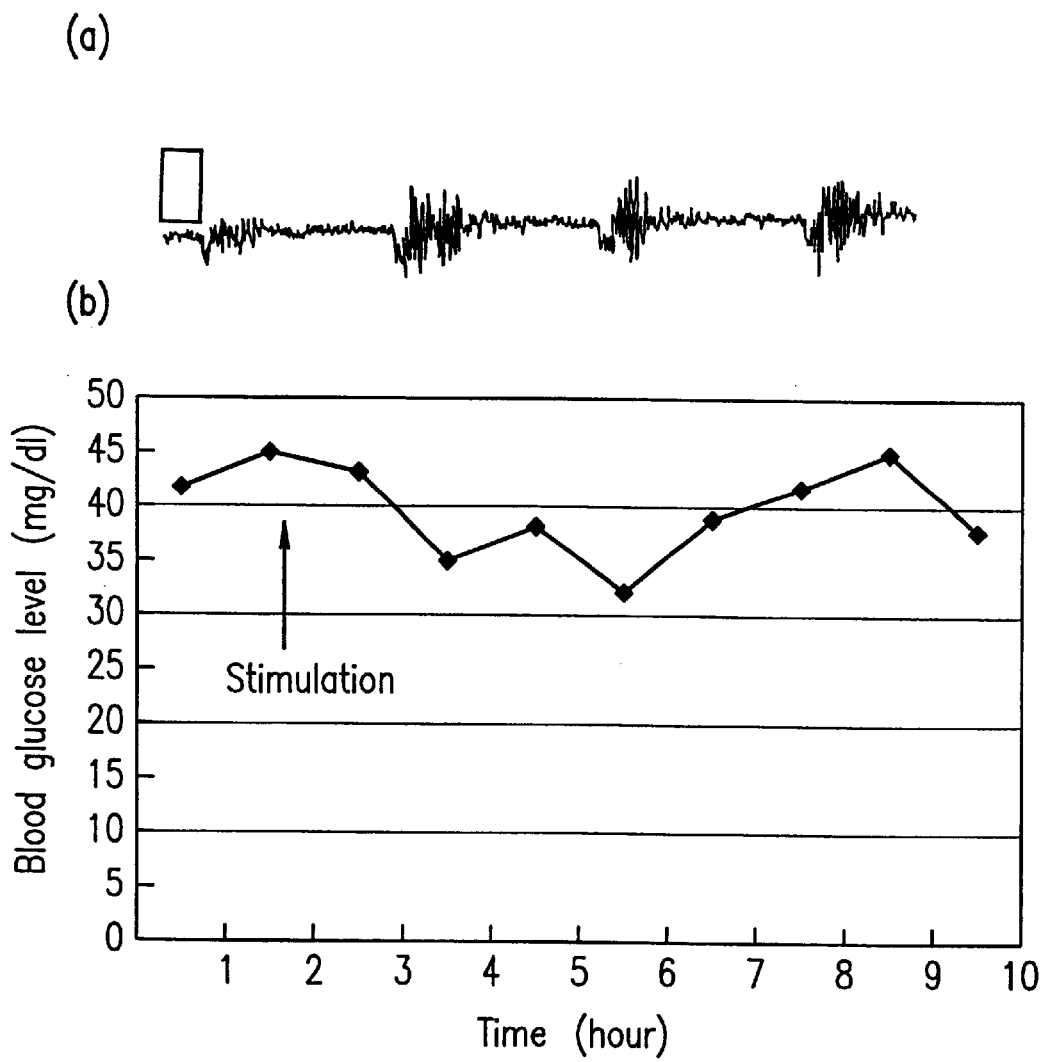
FIG. 9 is a graph showing a variation of the blood glucose level of a rat against time. Section (a) shows an electrical signal pattern which was supplied to the measuring electrode portion in Example 3; and section (b) is a graph showing variation of the blood glucose level of a rat against time when the electrical signal pattern of section (a) was supplied to the measuring electrode portion.
Figure 10:
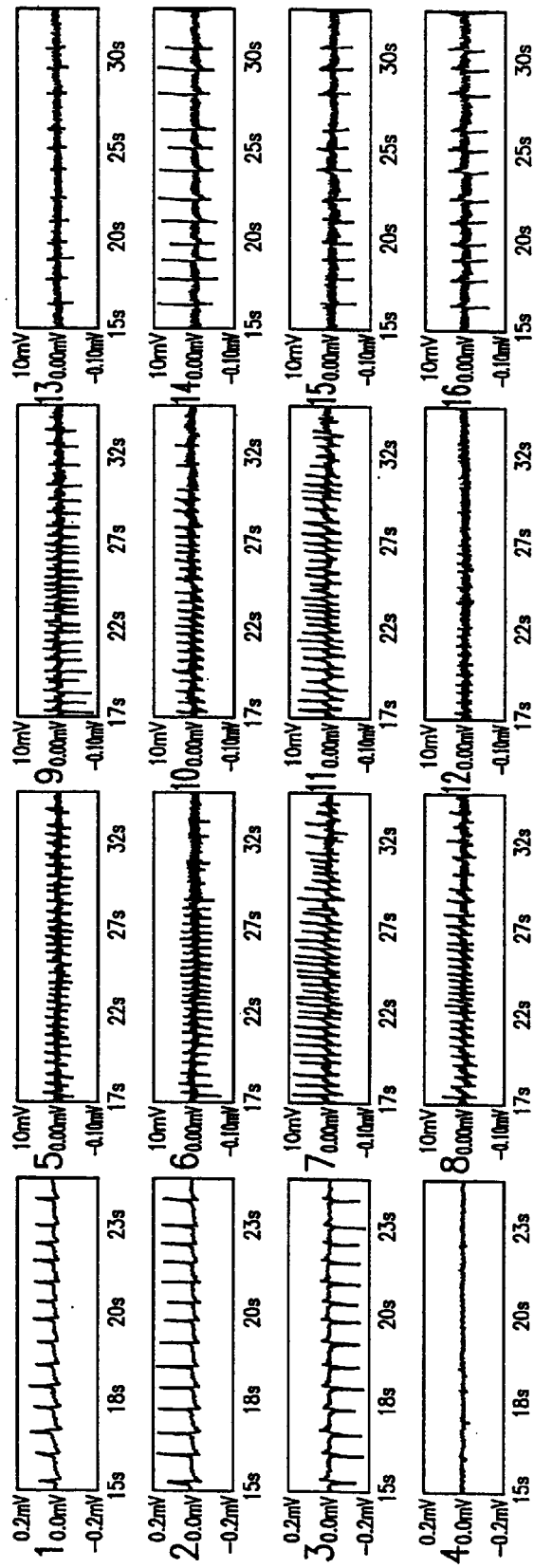
FIG. 10 shows an electrical signal pattern measured by the measuring electrode portion in Example 4.

By supplying the electrical signals shown in FIG. 7 to the respective micro electrodes 13 of the measuring electrode portion 10, the blood pressure and the heart rate were increased. As shown in FIG. 8, the blood pressure reached its maximum value about one hour after the application of the electrical signals, and the heart rate reached its maximum value about two hours after the application of the electrical signals.

Thus, it was confirmed that brain cells were activated by supplying predetermined electrical signal patterns to the olfactory bulb, so that physiological responses, i.e., increases in the blood pressure and the heart rate, were induced.

Example 3

The measuring electrode portion 10 shown in FIG. 2 was attached to a rat in a similar manner to that described in Example 1. Each micro electrode 13 of the measuring electrode portion 10 was made of ITO, which is a conductive material. The surface of each micro electrode 13 was plated with gold. As the substrate 12, a polyimide film material having a thickness of 100 μm was used.

The rat with the measuring electrode portion 10 attached thereto was fixed in the test animal fixing device 32 of the screening apparatus 1 shown in FIG. 1. The electrical signal shown in section (a) of FIG. 9 were supplied to the measuring electrode portion 10 such that a stimulation pattern was supplied to the olfactory bulb of the rat. A variation in the blood glucose level of the rat with the passage of time, which was caused when such an electrical signal pattern was supplied to the measuring electrode portion 10, was measured. The result of the measurement is shown in section (b) of FIG. 9.

Thus, it was confirmed that, when the predetermined electrical signal pattern was supplied to the olfactory bulb, a physiological response, i.e., a decrease in the blood glucose levels, was induced.

Example 4

The measuring electrode portion 10 shown in FIG. 4 was attached to a rat in a similar manner to that described in Example 1. The needle-shaped conductive leads 16 of the measuring electrode portion 10 were made of platinum, which is a conductive material. The conductive leads 16 of the conductive material were insulatively covered with polyimide. The diameter of the needle-shaped conductive lead 16 was 100 μm, and the interval between adjacent micro electrodes 16a in the electrode column 17 was 500 μm. The micro electrode 16a was covered with a thin film of collagen in order to improve adhesiveness of the micro electrode 16a to a biomedical tissue.

The rat with the measuring electrode portion 10 attached thereto was fixed in the test animal fixing device 32 of the screening apparatus 1 shown in FIG. 1. The electrical signals shown in FIG. 10 were supplied to the respective sixteen micro electrodes 16a of the measuring electrode portion 10 in a typical environment in which the rat lives. Variations in the blood pressure and the heart rate, which were caused when stimulation patterns of the electrical signals were supplied to the olfactory bulb, were measured for both a low oxygen concentration condition and a high oxygen concentration condition. In the low oxygen concentration condition, the oxygen concentration was 5% lower than that of normal air. In the high oxygen concentration condition, the oxygen concentration was 5% higher than that of normal air. The results of the measurement is shown in FIG. 11.

Figure 11:
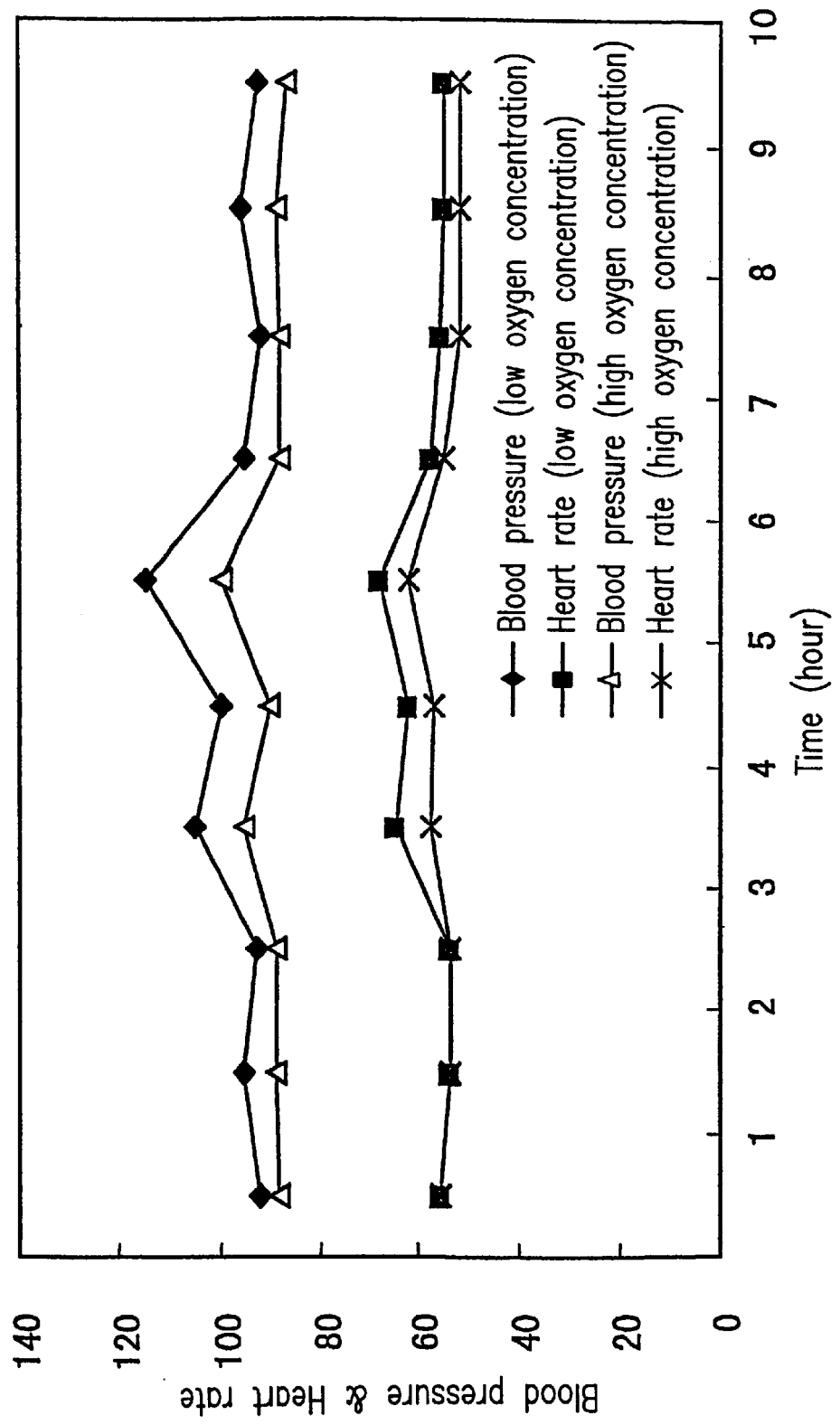
FIG. 11 is a graph showing variations of blood pressure and heart rate against time which were measured in Example 4.

As shown in FIG. 11, the electrical signal patterns supplied to the olfactory bulb induced physiological changes, i.e., increases in the blood pressure and the heart rate. Further, it was confirmed that both the blood pressure and the heart rate of the rat were increased more greatly under the low oxygen concentration condition rather than under the high oxygen concentration condition.

The same measurement results were obtained even when the measuring electrode portion 10 shown in FIG. 3 was used in place of the measuring electrode portion 10 shown in FIG. 4.

In this example, the measuring electrode portion 10 used has a plurality of micro electrodes on both the front and back surfaces thereof. However, an electrode portion having electrodes only on the front surface can be used to only detect a signal for screening.

As described in each of Examples 1–4, according to an apparatus and method of the present invention, a physiological response is induced by stimulating an olfactory bulb of an organism. Further, different stimulation patterns supplied to the olfactory bulb induce different types of, or different levels of, physiological responses. Thus, olfactory mucosa stimulating compounds are screened based on the correlation with the type, level, etc., of the physiological response induced when the olfactory mucosa stimulating compound stimulates the olfactory mucosa of an organism.

The olfactory mucosa stimulating compounds so identified have immediate efficacy because they act directly on brain cells. Further, such compounds can be used as novel drugs which can be administered into a patient who cannot accept drug administration such as oral administration, intravenous injection, intramuscular injection, etc. Furthermore, according to the present invention, it is possible to create drugs which are effective against new diseases which may emerge as a result of various changes in the environment.

Furthermore, an electrical signal pattern, which may be induced in an olfactory bulb in response to a stimulation of the olfactory bulb that is produced by an olfactory mucosa stimulating compound, and the type, level, etc., of a physiological response induced by the electrical signal pattern, may be stored as data. Based on such data, a stimulation pattern which induces a predetermined physiological response can be supplied, in the form of an electrical signal pattern, to the measuring electrode portion attached to the olfactory bulb of an organism, whereby the predetermined physiological response is induced in the organism. In this way, treatment of the organism, such as a decrease in the blood pressure, a decrease in the blood glucose level, or the like, can be achieved.

Each of above Examples 1–4 is merely an example employed for demonstrating availability of an apparatus and method of the present invention. The present invention is not limited to the above supplied compound, oxygen concentrations, or the like.

Hereinabove, the present invention has been described by way of examples. However, the present invention is not limited to such examples, but can be carried out in the form of variously changed, modified, or altered embodiments based on the knowledge of those skilled in the art within the scope of the present invention.

INDUSTRIAL APPLICABILITY

In a screening apparatus and method of the present invention, an electrical signal which is generated by an olfactory mucosa stimulating compound is measured by a measuring electrode portion implanted in an olfactory mucosa of a test animal, and a physiological response induced in the test animal concurrently with the electrical signal is detected. Based on the physiological response induced in the test animal, efficacy of the olfactory mucosa stimulating compound is determined. Thus, olfactory mucosa stimulating compounds effective for a test animal can be readily and reliably screened.

Furthermore, a treatment apparatus of the present invention supplies a stimulation directly to brain cells of a human. Thus, in this treatment apparatus, there is no possibility that side effects are caused, which may be caused by administration of a drug. Further still, a measuring electrode portion of the present invention can be preferably used in the above screening apparatus and treatment apparatus.

What is claimed is:

1. An exemplary olfactory mucosa stimulating compound screening apparatus, comprising:

an administration means for administering an olfactory mucosa stimulating compound toward an olfactory mucosa of a test animal;

a measuring electrode portion implanted in an olfactory bulb of the test animal for measuring an electrical signal generated in the olfactory bulb; and a processing means for analyzing a correlation between an electrical signal measured by the measuring electrode portion when the olfactory mucosa stimulating compound is administered to the olfactory mucosa of the test animal by the administration means and a physiological response induced in the test animal.

2. An exemplary olfactory mucosa stimulating compound screening apparatus according to claim 1, wherein the processing means directly obtains data concerning the physiological response from the test animal, so as to analyze the correlation between the physiological response and the electrical signal obtained by the measuring electrode portion.

3. An exemplary olfactory mucosa stimulating compound screening apparatus according to claim 1, wherein the processing means previously stores data concerning an electrical signal in the olfactory bulb which induces a physiological response in the test animal, and analyzes based on the data the correlation between a physiological response and an electrical signal obtained by the measuring electrode portion.

4. An exemplary olfactory mucosa stimulating compound screening apparatus according to claim 1, wherein the administration means includes a box for containing the olfactory mucosa stimulating compound, and a nozzle for spraying the olfactory mucosa stimulating compound con tained in the box in the vicinity of the olfactory mucosa of the test animal.

5. An exemplary olfactory mucosa stimulating compound screening apparatus according to claim 1, wherein the measuring electrode portion has at least one micro electrode for detecting an electrical signal from a nerve cell of the olfactory bulb.

6. An exemplary olfactory mucosa stimulating compound screening apparatus according to claim 5, wherein the measuring electrode portion has a plurality of micro electrodes, the microelectrodes being arranged such that an electrical signal pattern generated in the olfactory bulb by administration of the olfactory mucosa stimulating compound to the olfactory mucosa of the test animal is obtained at a plurality of points.

7. An exemplary olfactory mucosa stimulating compound screening apparatus according to claim 5, wherein an electrical signal which induces a physiological response in the test animal is supplied to each of the micro electrodes.

* * * * *

UNITED STATES PATENT AND TRADEMARK OFFICE
CERTIFICATE OF CORRECTION

| | |
|---|---|
| PATENT NO. | : 6,994,671 B2 |
| APPLICATION NO. | : 10/070170 |
| DATED | : February 7, 2006 |
| INVENTOR(S) | : Hiroaki Oka et al. |

It is certified that error appears in the above-identified patent and that said Letters Patent is hereby corrected as shown below:

Delete the word "exemplary" in Line 1 of each of Claims 1 through 7 which begin at Column 16, line 33.

Signed and Sealed this

Fifth Day of December, 2006

JON W. DUDAS
*Director of the United States Patent and Trademark Office*

UNITED STATES PATENT AND TRADEMARK OFFICE
CERTIFICATE OF CORRECTION

PATENT NO.       : 6,994,671 B2
APPLICATION NO.  : 10/070170
DATED            : February 7, 2006
INVENTOR(S)      : Hiroaki Oka et al.

It is certified that error appears in the above-identified patent and that said Letters Patent is hereby corrected as shown below:

Col. 16, line 33 delete "exemplary".
line 48 delete "exemplary".
line 55 delete "exemplary".
line 63 delete "exemplary".

Col. 17, line 3 delete "exemplary".
line 8 delete "exemplary".

Col. 18, line 5 delete "exemplary".

Signed and Sealed this

Second Day of January, 2007

JON W. DUDAS
*Director of the United States Patent and Trademark Office*